(12) United States Patent
Dolan et al.

(10) Patent No.: US 9,855,074 B2
(45) Date of Patent: Jan. 2, 2018

(54) ADJUSTABLE MEDICAL DEVICES AND METHODS FOR MANIPULATING BODILY TISSUES

(71) Applicant: Boston Scientific Scimed, Inc., Maple Grove, MN (US)

(72) Inventors: Andrew Dolan, Bridgewater, MA (US); Kenneth M. Flynn, Woburn, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 153 days.

(21) Appl. No.: 14/567,880

(22) Filed: Dec. 11, 2014

(65) Prior Publication Data

US 2015/0164553 A1    Jun. 18, 2015

Related U.S. Application Data

(60) Provisional application No. 61/915,796, filed on Dec. 13, 2013.

(51) Int. Cl.
| | |
|---|---|
| *A61B 17/42* | (2006.01) |
| *A61B 17/46* | (2006.01) |
| *A61D 1/10* | (2006.01) |
| *A61B 17/02* | (2006.01) |
| *A61B 17/00* | (2006.01) |

(52) U.S. Cl.
CPC .......... *A61B 17/42* (2013.01); *A61B 17/0218* (2013.01); *A61B 2017/00557* (2013.01); *A61B 2017/4216* (2013.01)

(58) Field of Classification Search
CPC ................ A61B 17/42; A61B 17/0218; A61B 2017/4216; A61B 2017/00557; A61B 2017/00805; A61F 2/0045
USPC .......................................................... 606/119
See application file for complete search history.

(56) References Cited

U.S. PATENT DOCUMENTS

| | | |
|---|---|---|
| 1,615,728 A | 1/1927 | Smith |
| 3,580,313 A | 5/1971 | McKnight |
| 4,048,987 A | 9/1977 | Hurson |
| 4,226,228 A | 10/1980 | Shin et al. |
| 4,241,912 A | 12/1980 | Mercer et al. |

(Continued)

FOREIGN PATENT DOCUMENTS

| | | |
|---|---|---|
| DE | 202004015215 U1 | 12/2004 |
| FR | 2817731 A1 | 6/2002 |

(Continued)

OTHER PUBLICATIONS

Final Office Action for U.S. Appl. No. 13/801,897, dated Aug. 25, 2016, 38 pages.

(Continued)

*Primary Examiner* — Katherine M Shi
(74) *Attorney, Agent, or Firm* — Brake Hughes Bellermann LLP

(57) ABSTRACT

A medical device includes an elongate member having a first end portion and a second end portion, an extension member movably coupled to the first end portion of the elongate member and an actuation member disposed on the second end portion of the elongate member and operatively coupled to the extension member to move the extension member from a first position with respect to the first end portion of the elongate member to a second position with respect to the elongate member.

13 Claims, 12 Drawing Sheets

(56) References Cited

U.S. PATENT DOCUMENTS

| | | | |
|---|---|---|---|
| 4,747,393 A | 5/1988 | Medwid | |
| 4,784,150 A | 11/1988 | Voorhies et al. | |
| 4,881,526 A | 11/1989 | Johnson et al. | |
| 5,209,754 A | 5/1993 | Ahluwalia | |
| 5,217,463 A | 6/1993 | Mikhail | |
| 5,318,013 A * | 6/1994 | Wilk | A61B 17/0218 128/898 |
| 5,483,832 A | 1/1996 | Pauser et al. | |
| 5,518,503 A | 5/1996 | Rooney et al. | |
| 5,520,703 A | 5/1996 | Essig et al. | |
| 5,665,072 A * | 9/1997 | Yoon | A61B 17/3417 604/164.12 |
| 5,785,640 A | 7/1998 | Kresch et al. | |
| 5,803,902 A | 9/1998 | Sienkiewicz | |
| 6,048,351 A | 4/2000 | Gordon et al. | |
| 6,068,591 A | 5/2000 | Bruckner et al. | |
| 6,165,108 A | 12/2000 | Ralston et al. | |
| 6,264,676 B1 | 7/2001 | Gellman et al. | |
| 6,394,939 B1 | 5/2002 | Stein et al. | |
| 6,485,500 B1 * | 11/2002 | Kokish | A61M 25/104 604/101.01 |
| 7,001,317 B2 | 2/2006 | Marcotte et al. | |
| 7,037,255 B2 | 5/2006 | Inman et al. | |
| 7,048,682 B2 | 5/2006 | Neisz et al. | |
| 7,371,245 B2 | 5/2008 | Evans et al. | |
| 7,611,454 B2 | 11/2009 | De et al. | |
| 7,981,024 B2 | 7/2011 | Levy | |
| 9,144,421 B1 * | 9/2015 | Lau | A61B 17/00 |
| 9,282,956 B2 | 3/2016 | Fairneny et al. | |
| 2002/0000233 A1 | 1/2002 | Jude et al. | |
| 2002/0022870 A1 * | 2/2002 | Truckai | A61B 18/1485 607/101 |
| 2002/0028980 A1 | 3/2002 | Thierfelder et al. | |
| 2002/0116025 A1 | 8/2002 | Haab | |
| 2004/0153065 A1 | 8/2004 | Lim | |
| 2005/0000523 A1 | 1/2005 | Beraud | |
| 2005/0131393 A1 | 6/2005 | Chu et al. | |
| 2005/0256530 A1 | 11/2005 | Petros et al. | |
| 2005/0277948 A1 | 12/2005 | Cedars et al. | |
| 2005/0278037 A1 | 12/2005 | Delorme et al. | |
| 2006/0058578 A1 | 3/2006 | Browning et al. | |
| 2006/0089525 A1 | 4/2006 | Mamo et al. | |
| 2006/0100475 A1 | 5/2006 | White et al. | |
| 2006/0195007 A1 | 8/2006 | Anderson et al. | |
| 2006/0217589 A1 | 9/2006 | Wan et al. | |
| 2006/0229596 A1 | 10/2006 | Weiser et al. | |
| 2007/0015953 A1 | 1/2007 | MacLean | |
| 2007/0060795 A1 | 3/2007 | Vayser et al. | |
| 2007/0112361 A1 | 5/2007 | Schonholz et al. | |
| 2007/0161849 A1 | 7/2007 | Goldberg | |
| 2008/0039678 A1 | 2/2008 | Montpetit et al. | |
| 2008/0081952 A1 | 4/2008 | Josephberg | |
| 2008/0221384 A1 | 9/2008 | Chi Sing et al. | |
| 2009/0171143 A1 | 7/2009 | Chu et al. | |
| 2009/0209973 A1 | 8/2009 | East | |
| 2009/0281377 A1 | 11/2009 | Newell et al. | |
| 2010/0063534 A1 * | 3/2010 | Kugler | A61B 17/221 606/200 |
| 2010/0137692 A1 | 6/2010 | Lindsay et al. | |
| 2010/0286482 A1 | 11/2010 | Rosenblatt | |
| 2010/0305394 A1 | 12/2010 | Rosenblatt | |
| 2010/0312051 A1 | 12/2010 | Brown et al. | |
| 2011/0295301 A1 * | 12/2011 | Hoem | A61B 5/0215 606/194 |
| 2012/0016185 A1 | 1/2012 | Sherts et al. | |
| 2012/0143209 A1 * | 6/2012 | Brecheen | A61B 17/42 606/119 |
| 2013/0005543 A1 | 1/2013 | Armitage et al. | |
| 2013/0035543 A1 | 2/2013 | Fischer et al. | |
| 2013/0072749 A1 * | 3/2013 | Fairneny | A61B 17/02 600/37 |
| 2013/0197537 A1 * | 8/2013 | Fairneny | A61B 17/42 606/119 |
| 2013/0274759 A1 * | 10/2013 | Oskin | A61B 17/42 606/119 |

FOREIGN PATENT DOCUMENTS

| | | |
|---|---|---|
| GB | 1604168 A | 12/1981 |
| WO | 2009076616 A2 | 6/2009 |
| WO | 2013040022 A1 | 3/2013 |
| WO | 2014143626 A1 | 9/2014 |

OTHER PUBLICATIONS

Search Report and Written Opinion for PCT Application No. PCT/US12/54844, dated Oct. 17, 2012, 31 pages.
Final Office Action for U.S. Appl. No. 13/610,285, dated Jan. 5, 2015, 24 pages.
Final Office Action U.S. Appl. No. 13/610,285, dated Aug. 28, 2015, 20 Pages.
Non Final Office Action U.S. Appl. No. 13/610,285, dated May 20, 2014, 17 pages.
Non-Final Office Action U.S. Appl. No. 13/610,285, dated Apr. 28, 2015, 19 pages.
Notice of Allowance U.S. Appl. No. 13/610,285, dated Nov. 4, 2015, 11 Pages.
Final Office Action U.S. Appl. No. 13/801,897, dated Aug. 28, 2015, 25 Pages.
Non-Final Office Action U.S. Appl. No. 13/801,897, dated Mar. 27, 2015, 21 pages.
First Examiner Report AU Application No. AU2012308754, dated Apr. 14, 2016, 4 pages.
International Preliminary Report on Patentability for PCT Application No. PCT/US12/54844, dated Mar. 27, 2014, 9 Pages.
International Preliminary Report on Patentability for PCT Application No. PCT/US2014/024814, dated Sep. 24, 2015, 11 Pages.
International Search Report and Written Opinion for PCT Application No. PCT/US2014/024814, dated May 9, 2014, 16 pages.
Puntambekar, et al., "A Novel Technique of UterineManipulation in Laparoscopic Pelvic Oncosurgical Procedures:"The Uterine Hitch Technique"", Nov. 26, 2009, 6 pages.

* cited by examiner

ADJUSTABLE MEDICAL DEVICES AND METHODS FOR MANIPULATING BODILY TISSUES

CROSS-REFERENCE TO RELATED APPLICATION

This application is a Nonprovisional of, and claims priority to, U.S. Patent Application No. 61/915,796, filed on Dec. 13, 2013, entitled "ADJUSTABLE MEDICAL DEVICES AND METHODS FOR MANIPULATING BODILY TISSUES", which is incorporated by reference herein in its entirety.

BACKGROUND

Field

The present invention generally relates to medical devices and procedures, particularly devices and methods used during surgery to manipulate bodily tissue.

Various types of tissue manipulators are used for manipulating pelvic and other organs to facilitate access to their anatomical structures during surgical procedures. A vaginal manipulator is one such manipulator that can be introduced into a vagina for manipulating vaginal tissues. Several vaginal manipulators are available to help maneuver the vagina or vaginal walls, facilitating proper dissection in the pelvis. The purpose of some vaginal manipulators is to move the vagina around so that it is easier for dissection and placement of various medical devices such as implants. The vaginal manipulator may also act as a stabilizing backstop for suturing during abdominal/laparoscopic pelvic floor procedures.

Various shapes of vaginal manipulators are available to meet the requirements of surgery. Some existing manipulators used in pelvic surgeries are round or cylindrical in shape at their distal ends and are configured to contact the vaginal tissues. Other existing manipulators include flat or planar surfaces with rounded or curved end portions. With these known devices, however, it may be difficult to insert the manipulators into the body of the patient. Additionally, with these known devices, it may be difficult to control or manipulate the cervix or the uterus when the vaginal manipulator is placed within the vagina of the patient.

Thus, there is a need for an improved medical device or manipulator such as a vaginal manipulator that allows for or helps facilitate the insertion process. Also, there is a need for an improved medical device or manipulator that allows for or helps provide for the controlling or manipulating of the cervix or uterus.

SUMMARY

In one embodiment, a medical device includes an elongate member having a first end portion and a second end portion, an extension member movably coupled to the first end portion of the elongate member and an actuation member disposed on the second end portion of the elongate member and operatively coupled to the extension member to move the extension member from a first position with respect to the first end portion of the elongate member to a second position with respect to the elongate member.

In another embodiment, A medical device includes an elongate member having a first end portion and a second end portion, the first end portion of the elongate member having a first side portion, a second side portion opposite the first end portion, and a terminal portion, the first end portion defining a cavity; an extension member movably coupled to the terminal portion of the first end portion of the elongate member, a portion of the extension member being disposed within the cavity when the extension member is in its first position, the portion of the extension member being disposed outside of the cavity when the extension member is in its second position; and an actuation member disposed on the second end portion of the elongate member and operatively coupled to the extension member to move the extension member from a first position with respect to the first end portion of the elongate member to a second position with respect to the elongate member.

In another embodiment, A method, includes inserting a medical device into a body of a patient, the medical device including an elongate member having a first end portion and a second end portion, an extension member movably coupled to the first end portion of the elongate member and configured to move from a first position with respect to the elongate member to a second position with respect to the elongate member; moving an actuator of the medical device to move the extension member from its first position to its second position; and engaging the extension member of the medical device with bodily tissue of the patient.

DETAILED DESCRIPTION

Figure 1:
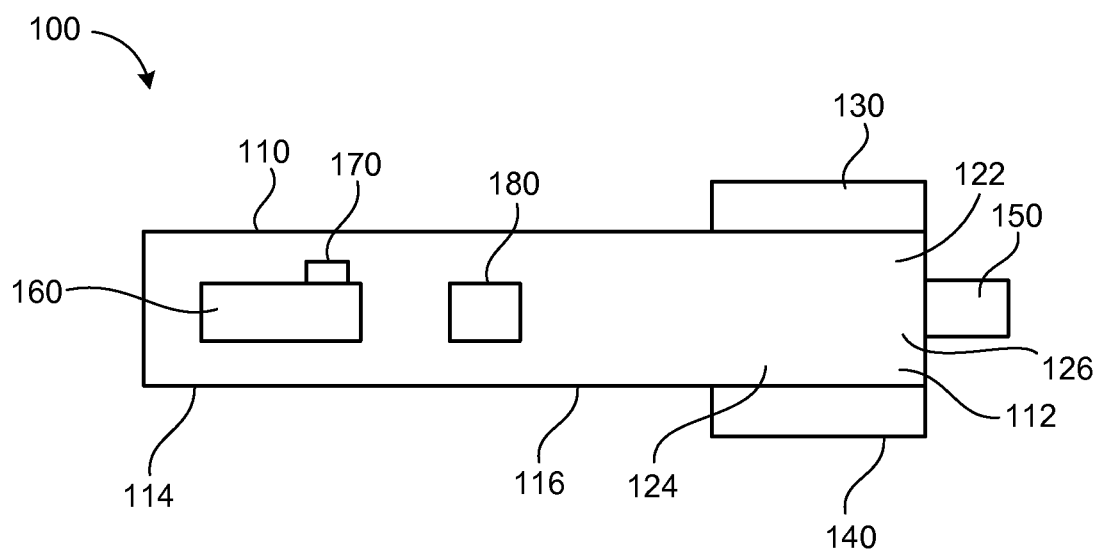
FIG. 1 is a schematic diagram of a medical device configured to manipulate a bodily tissue, in accordance with an embodiment of the invention.

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "operatively coupled," as used herein, is defined as connected, although not necessarily directly and mechanically.

In general, the invention is directed to systems, methods, and devices for treating female pelvic prolapse. However, the invention can be equally employed for other treatment purposes such as anal prolapse in males or females and for rectal manipulation during ano-rectosigmoid resections and other pelvic surgeries in which rectal manipulation is required. As described below in various illustrative embodiments, the invention provides systems, methods, and devices employing an improved manipulator configured to help maneuver the vagina facilitating proper dissection in the pelvis. The purpose of the vaginal manipulator is to move the vagina, cervix, and/or uterus around so that it is easier for dissection and placement of various implants into a patient's body. The vaginal manipulator may also acts as a backstop for suturing during abdominal/laparoscopic pelvic floor procedures.

The term patient may hereafter be used for a person who benefits from the medical device or the methods disclosed in the present invention. For example, the patient can be a person whose body is operated through the medical device or the method disclosed by the present invention. For example, in some embodiments, the patient may be a human female, a human male, or any other mammal.

The terms proximal and distal described in relation to various devices, apparatuses, and components as discussed in the subsequent text of the present invention are referred with a point of reference. The point of reference, as used in this description, is a perspective of an operator. The operator may be a surgeon, a physician, a nurse, a doctor, a technician, and the like, who may perform the procedure and operate the medical device as described in the present invention. The term proximal refers to an area or portion that is closer or closest to the operator during a surgical procedure. The term distal refers to an area or portion that is farther or farthest from the operator.

FIG. 1 is a schematic diagram of a medical device 100 configured to manipulate a portion of a body of a patient such as bodily tissue or other member or portion of the body. Medical devices described herein may be used to manipulate any portion of a body of a patient, including but not limited to, the vagina, uterus, bladder, stomach, intestines, lungs, peritoneum, abdomen, and so forth. The medical device 100 includes an elongated member 110. The elongate member has a first end portion 112 and a second end portion 114. In some embodiments, the first end portion 112 is disposed opposite the second end portion 114. In some embodiments, the elongate member 110 includes a shaft portion 116 that is disposed between the first end portion 112 and the second end portion 114. In some embodiments, the shaft portion 116 is linear. In other embodiments, the shaft portion 116 is curved or includes a curved portion.

In some embodiments, the first end portion 112 of the medical device 100 includes surfaces that are configured to help maneuver the vagina to facilitate proper dissection in the pelvis. In some embodiments, flat surfaces of the first end portion 112 are configured to contact and move the vagina around so that it is easier for dissection and placement of implants such as suspension implant or devices such as the sacrocolpopexy mesh arms. Flat or planar surfaces of the first end portion 112 may also act as a backstop for suturing during abdominal/laparoscopic pelvic floor procedures. The flat surfaces can also be used to spread the bodily tissue to facilitate suturing at a correct location. In some embodiments, the medical practitioner may use a first flat surface to suture on anterior portions of the vagina and a second flat surface to suture on posterior portions of the vagina.

In the illustrated embodiment, extension or expansion members 130, 140, and 150 are coupled to the first end portion 112. Specifically, the first extension or expansion member 130 is movably coupled to a first side portion 122 of the first end portion 112. The first extension member 130 is configured to move with respect to the first end portion 112. For example the first extension member 130 may move away from (or perpendicular to) a longitudinal axis of the elongate member 110 when the first extension member 130 moves from a first position with respect to the first end portion 112 to a second position with respect to the first end portion 112. In such embodiments, the width or size of the first end portion 112 and the first extension member 130 may be varied. Accordingly, the device 100 may be inserted into the body of the patient when the first extension member 130 is in one position (a retracted or smaller configuration) and may be moved to the other position (an expanded or larger configuration) when the device 100 is within the body of the patient. Additionally, in some embodiments, the device 100 may be removed from the body of the patient when the first extension member 130 is in its retracted or smaller configuration. In some embodiments, the first extension member 130 may be placed in more than two positions with respect to the first end portion 112. For example, in some embodiments, the first extension member 130 may be placed in three, four, or more different positions with respect to the first end portion 112.

The second extension or expansion member 140 may be similar to the first extension member 130. The second extension member 140 is movably coupled to a second side portion 124 of the first end portion 112. The second extension member 140 is configured to move with respect to the first end portion 112. For example the second extension member 140 may move away from (or perpendicular to) a longitudinal axis of the elongate member 110 when the second extension member 140 moves from a first position with respect to the first end portion 112 to a second position with respect to the first end portion 112. In such embodiments, the width or size of the first end portion 112 and the second extension member 140 may be varied. Accordingly, the device 100 may be inserted into the body of the patient when the second extension member 140 is in one position (a retracted or smaller configuration) and may be moved to the other position (an expanded or larger configuration) when the device 100 is within the body of the patient.

In the some embodiments, the device 100 (or at least the first end portion 112 of the device 100) may be inserted into the body of the patient when both the first extension member 130 and the second extension member 140 are in their retracted positions or configurations. Once the device 100 is disposed within the body of the patient, the first extension member 130 and the second extension member 140 may be moved to their extended or expanded positions with respect to the first end portion 112. Following the procedure, the first extension member 130 and the second extension member 140 may be moved back to their retracted positions or configurations and the device 100 may be removed from the body of the patient.

The third extension or expansion member 150 is movably coupled to a distal or terminal end portion 126 of the first end portion 112. The third extension member 150 is configured to move with respect to the first end portion 112. For example, the third extension member 150 may move parallel to a longitudinal axis of the elongate member 110 when the third extension member 150 moves from a first position with respect to the first end portion 112 to a second position with respect to the first end portion 112. In such embodiments, the length or size of the first end portion 112 and the extension member 150 may be varied. Accordingly, the device 100 may be inserted into the body of the patient when the third extension member 150 is in one position (a retracted or smaller configuration) and may be moved to the other position (an expanded or larger configuration) when the device 100 is within the body of the patient.

In some embodiments, more than one extension or expansion member may be disposed on the same side or portion of the first end portion 112. In some embodiments, the extension or expansion members may include balloons, cages (such as basket-like cages), malecot baskets, bellow, rack and pinion systems, hinged wings, folding portions, stacked or telescoping portions, wedges, sliding coplanar portions, unfurled or unrolled portions, and the like and combinations thereof. The extension or expansion members may have any shape including flat, curved, wavy, bulbous, angled, tapered, coplanar, multiplanar, and the like and combinations thereof. The corners of the extension or expansion members may be radiused, sharp, notched or the like.

In some embodiments, the extension or expansion members may be configured to move in more than one direction. For example, the extension or expansions members may be configured to move distally and sideways with resect to the first end portion. In some embodiments, the extension or expansion members may be configured to move in more than one plane.

In the illustrated embodiment, the device 100 includes an actuator or actuation member 160. The actuator 160 is operatively coupled to the first extension member 130. The actuator 160 may be moved or otherwise actuated to cause the first extension member 130 to move from its first position with respect to the first end portion 112 to its second position with respect to the first end portion 112. In some embodiments, the actuator 160 may be operatively coupled to and be configured to move the second extension member 140 and the third extension member 150 to their expanded positions or configurations. In other embodiments, the device 100 includes additional actuators that are configured to move or cause the second extension member 140 and the third extension member to their expanded positions or configurations.

In some embodiments, the actuation of the actuator may occur in any manner. For example, in some embodiments, the actuator or actuation member 160 may be actuated by sliding, rotating, or bending the actuation member 160 in any direction. The actuation may be manual or may be mechanically assisted (such as via a spring or other mechanical member). Additionally, the actuation member 160 may be reset manually or with mechanical assistance.

In some embodiments, the movement of the extension or expansion members may occur in a series of discrete steps. For example, each step the extension or expansion members may extend further from the first end portion until a maximum distance is achieved.

In some embodiments, the actuation member is disposed within a lumen defined by a handle of the device. In other embodiments, the actuation member may be disposed along or on a surface of the handle (for example, within a groove or slot defined by the handle). In other embodiments, the actuation member may be disposed on a sheath.

In the illustrated embodiment, the device 100 includes a lock member or lock mechanism 170. The lock member or lock mechanism 170 is operatively coupled to the actuator 160 or the first extension member 130 and is configured to lock or help retain the first extension member in one of its first position and its second position with respect to the first end portion 112.

In the illustrated embodiment, the device 100 includes a release member or release mechanism 180. The release member or release mechanism 180 is operatively coupled to the lock member or lock mechanism 170 and is configured to release the lock member or lock mechanism from engagement with the actuator 160 or the first extension member 130. Accordingly, the release member 180 may be actuated when lock member is retaining the first extension member 130 in one of its first position and its second position to release the first extension member 130 such that it is free to move between its first position and its second position.

In some embodiments, the first extension member 130 is biased to its retracted configuration. For example, the first extension member 130 may be spring biased to its retracted position or configuration. The device 100 may be inserted into the body of the patient while the first extension member 130 is in its retracted position. Specifically, the device 100 may be inserted into the body of the patient while the first extension member 130 is in its retracted configuration such that the first end portion 112 of the device 100 is disposed within the body of the patient (such as within a vagina or other bodily opening of the patient) and the second end portion 114 of the device extends from the body of the patient. The actuator 160 (which may be disposed on the second end portion 114 of the device) may then be activated to cause the first extension member 130 to move to its expanded configuration. The lock member 170 may retain the first extension member 130 in its expanded configuration and a medical procedure may be performed on the patient. Once the procedure is completed, the release member 180 (which may be disposed on the second end portion 114 of the device) may be activated to release the first extension member 130 and allow it to move back to its first position or configuration. The device 100 may then be removed from the body of the patient while the first extension member is in its retracted or smaller configuration.

Figure 2A:
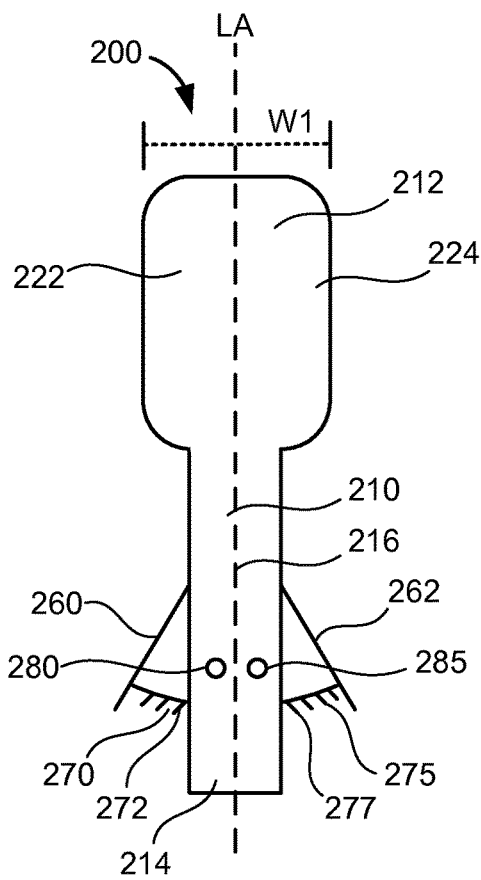
FIG. 2A is a top view of a medical device according to an embodiment of the invention in a first or retracted configuration.
Figure 2B:
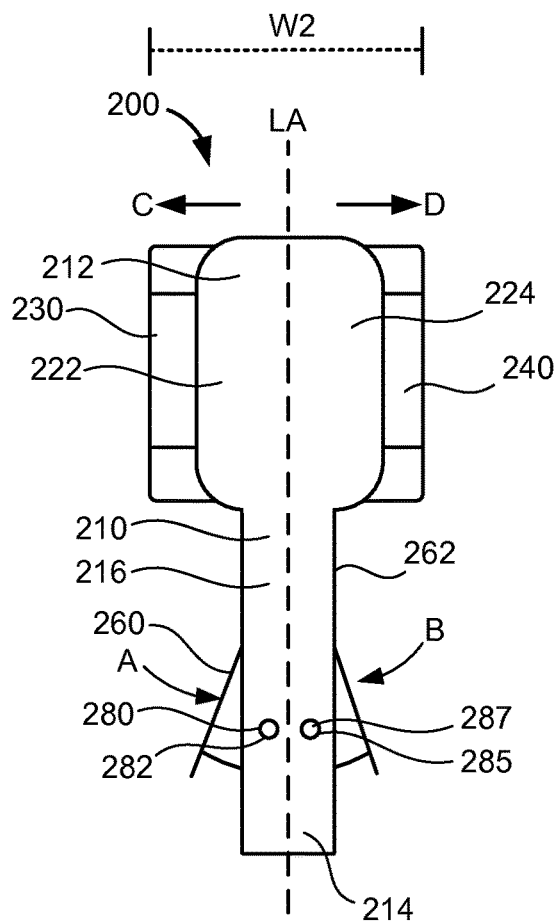
FIG. 2B is a top view of the medical device of FIG. 2A in a second or expanded configuration.

FIGS. 2A and 2B are top views of a medical device 200 according to an embodiment of the invention. The medical device 200 is configured to manipulate a portion of a body of a patient such as bodily tissue or other member or portion of the body. The medical device 200 includes an elongate member 210. The elongate member has a first end portion 212 and a second end portion 214. In some embodiments, the first end portion 212 is disposed opposite the second end portion 214. The elongate member 210 also includes a shaft portion that is disposed between the first end portion 212 and the second end portion 214.

The first end portion 212 of the medical device 200 includes surfaces that are configured to help maneuver the vagina to facilitate proper dissection in the pelvis. The surfaces of the first end portion 112 may also act as a backstop for suturing during abdominal or laparoscopic pelvic floor procedures. The surfaces can also be used to spread the bodily tissue to facilitate suturing at a correct location. In some embodiments, the medical practitioner may use a first surface to suture on anterior portions of the vagina and a second surface (such as the surface opposite the first surface) to suture on posterior portions of the vagina.

In the illustrated embodiment, extension members 230 and 240 are coupled to the first end portion 212. Specifically, the first extension member 230 is movably or slidably coupled to a first side portion 222 of the first end portion 212. The first extension member 230 is configured to move with respect to the first end portion 212. Specifically, the first extension member 230 moves away from (or perpendicular to) a longitudinal axis LA of the elongate member 210 when the first extension member 230 moves from a first position with respect to the first end portion 212 to a second position with respect to the first end portion 212. Accordingly, the width or size of the first end portion 212 and the first extension member 230 may be varied. In some embodiments, the first extension member 230 (or a portion of the first extension member 230) is disposed within a cavity defined by the first end portion 212 when the first extension member 230 is in its retraced configuration. The first extension member 230 (or the portion of the first extension member 230) is disposed outside of the cavity defined by the first end portion 212 when the first extension member 230 is in its second or extended position.

The first extension member 230 may be placed in more than two positions with respect to the first end portion 212. For example, in some embodiments, the first extension member 230 may be placed in three, four, or more different positions with respect to the first end portion 212. Accordingly, the width or size of the first end portion 212 may be varied among many different sizes or widths.

The second extension member 240 may be similar to the first extension member 230. The second extension member 240 is movably coupled to a second side portion 224 of the first end portion 212. The second extension member 240 is configured to move with respect to the first end portion 212. Specifically, the second extension member 240 moves away from (or perpendicular to) the longitudinal axis LA of the elongate member 210 when the second extension member 240 moves from a first position with respect to the first end portion 212 to a second position with respect to the first end portion 212. Accordingly, the width or size of the first end portion 212 and the second extension member 240 may be varied. In some embodiments, the second extension member 240 (or a portion of the second extension member 240) is disposed within a cavity defined by the first end portion 212 when the second extension member 240 is in its retraced configuration. The second extension member 240 (or the portion of the second extension member 240) is disposed outside of the cavity defined by the first end portion 212 when the second extension member 240 is in its second or extended position.

The second extension member 240 may be placed in more than two positions with respect to the first end portion 212. For example, in some embodiments, the second extension member 240 may be placed in three, four, or more different positions with respect to the first end portion 212. Accordingly, the width or size of the first end portion 212 may be varied among many different sizes or widths.

In the some embodiments, the device 200 (or at least the first end portion 212 of the device 200) may be inserted into the body of the patient when both the first extension member 230 and the second extension member 240 are in their retracted positions or configurations with respect to the first end portion 212 (as illustrated in FIG. 2A). In this configuration, the device 200 has a first width W1. Once the device 200 is disposed within the body of the patient, the first extension member 230 and the second extension member 240 may be moved to their extended or expanded positions with respect to the first end portion 212 (as illustrated in FIG. 2B) In this configuration, the device 200 has a second width W2. The second width W2 is larger than the first width W1. Once the medical procedure is completed, the first extension member 230 and the second extension member 240 may be moved back to their retracted positions or configurations and the device 200 may be removed from the body of the patient.

In the illustrated embodiment, the device 200 includes a first actuator 260 and a second actuator 262. The first actuator 260 and the second actuator 262 are disposed on the second end portion 214 of the elongate member 210 and are configured to move with respect to the second end portion 214 (or the handle of the device 200). For example, a physician may operate, actuate, or move the first actuator 260 and the second actuator 262 by moving the first actuator 260 in the direction of arrow A in FIG. 2B. The physician may operate, actuate, or move the second actuator 262 to in the direction of arrow B in FIG. 2B.

The first actuator 260 is operatively coupled to the first extension member 230. The actuator 260 may be moved or otherwise actuated to cause the first extension member 230 to move from its first position with respect to the first end portion 212 to its second position with respect to the first end portion 212. In the illustrated embodiment, actuation of the first actuator 260 in the direction of arrow A causes the first extension member to move in the direction of arrow C to its expanded configuration. In some embodiments, linkages or other connection arms may be disposed within a cavity defined by the elongate member 210 to operatively couple the first actuator 260 to the first extension member 230.

Figure 3:
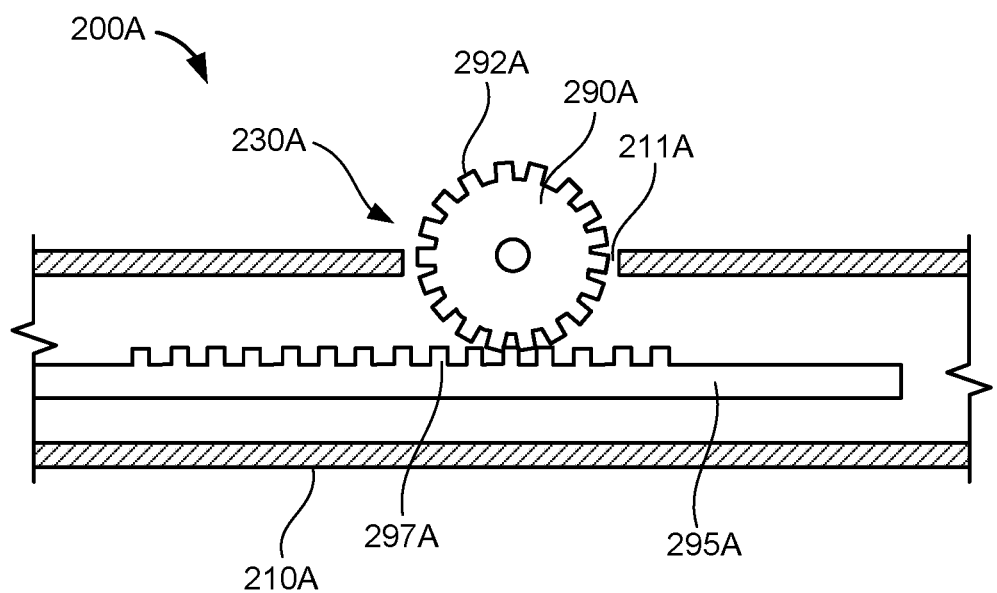
FIG. 3 is a cross-section view of a portion of a device according to an embodiment of the invention.

FIG. 3 is a cross-sectional view of a portion of a medical device 210A. As best illustrated in FIG. 3, in some embodiments, the actuator 230A of a medical device 200A may include a wheel 290A and a linkage 295A. The wheel 290A is rotatably coupled to the elongate member 210A and is positioned such that a portion of the wheel 290A extends from an opening 211A defined by the elongate member 210A. The wheel 290A is configured to engage the linkage 295A such that when the wheel 290A is rotated with respect to the elongate member 210A, the linkage 295A (which is disposed within a lumen defined by the elongate member 210A) is moved with respect to the elongate member 210A. Specifically, the wheel 290A includes or defines a set of teeth or projections 292A that engage a set of teeth or projections 297A of the linkage 295A. The teeth or projections 292A of the wheel 290A engage the teeth or projections 297A of the linkage 295A to cause the linkage 295A to move when the wheel 290A is rotated. The linkage 295 is moved in a first direction when the wheel 290A is rotated in a first direction and is moved in a second opposite direction when the wheel 290A is rotated in an opposite direction.

In the embodiment illustrated in FIG. 3, the linkage 295A may be coupled, either directly or via additional linkages, to the first extension member and the second extension member. Specifically, the linkage 295A may be coupled to the first extension member and to the second extension member such that when the linkage 295A moves in a first direction the first and second extension members are moved to their extended or expanded configurations. Additionally, movement of the linkage 295A in a second or opposite direction may cause the first and second extension members to move to their retracted configurations. Accordingly, the wheel 290A and the linkage 295A may be used to expand or contract the device 200A. Operation of the wheel 290A may be by direct hand contact or by an overlaid sliding component which slides relative to 210A and rotates the wheel 290A.

Returning to FIGS. 2A and 2B, the device 200 includes a first lock member or lock mechanism 270. The first lock member or lock mechanism 270 is operatively coupled to the first actuator 260 and the first extension member 230. The first lock member or mechanism 270 is configured to lock or help retain the first extension member 230 in one of its first position and its second position with respect to the first end portion 212. For example, in the illustrated embodiment, the first lock mechanism 270 is a ratchet mechanism that includes teeth or gears 272 that are configured to engage the elongate member 210 or a portion of the elongate member 210 to lock or help retain the first extension member 230 in its expanded configuration.

The device 200 includes a first release member or release mechanism 280. The first release member or release mechanism 280 is operatively coupled to the first lock member or lock mechanism 270 and is configured to release the first lock member or lock mechanism 270 from engagement with the first actuator 260 or the first extension member 230. Accordingly, the first release member 280 may be actuated when the first lock member is retaining the first extension member 230 in one of its first position and its second position to release the first extension member 230 such that it is free to move between its first position and its second position. In the illustrated embodiment, the first release member or release mechanism 280 includes a button 282 that may be depressed to release the lock member 270.

The second actuator 262 is operatively coupled to the second extension member 240. The second actuator 262 may be moved or otherwise actuated to cause the second extension member 240 to move from its first position with respect to the first end portion 212 to its second position with respect to the first end portion 212. In the illustrated embodiment, actuation of the second actuator 262 in the direction of arrow B causes the second extension member 240 to move in the direction of arrow D to its expanded configuration. In some embodiments, linkages or other connection arms may be disposed within a cavity defined by the elongate member 210 to operatively couple the second actuator 262 to the second extension member 240.

The device 200 includes a second lock member or lock mechanism 275. The second lock member or lock mechanism 270 is operatively coupled to the second actuator 262 and the second extension member 240. The second lock member or mechanism 275 is configured to lock or help retain the second extension member 240 in one of its first position and its second position with respect to the first end portion 212. For example, in the illustrated embodiment, the second lock mechanism 275 is a ratchet mechanism that includes teeth or gears 277 that are configured to engage the elongate member 210 to lock or help retain the second extension member 240 in its expanded configuration.

The device 200 includes a second release member or release mechanism 285. The second release member or release mechanism 285 is operatively coupled to the second lock member or lock mechanism 275 and is configured to release the second lock member or lock mechanism 275 from engagement with the second actuator 262 or the second extension member 240. Accordingly, the second release member 285 may be actuated when the second lock member 275 is retaining the second extension member 240 in one of its first position and its second position to release the second extension member 240 such that it is free to move between its first position and its second position. In the illustrated embodiment, the second release member or release mechanism 285 includes a button 287 that may be depressed to release the second lock member 275.

In some embodiments, the device 200 includes a single release mechanism that is operatively coupled to both the first lock member 270 and the second lock member 275. Actuation of the single release mechanism is causes the release of both the first lock member 270 and the second lock member 275 and allows both the first extension member 230 and the second extension member 240 to freely move between their first positions and their second positions.

In some embodiments, the extension members 230 and 240 are biased to their retracted configurations. For example, the extension members 230 and 240 may be spring biased to their retracted positions or configurations. The device 200 may be inserted into the body of the patient while the extension members 230 and 240 are in their retracted positions. Specifically, the device 200 may be inserted into the body of the patient while the extension members 230 and 240 are in their retracted configurations such that the first end portion 212 of the device 200 is disposed within the body of the patient (such as within a vagina or other bodily opening of the patient) and the second end portion 214 of the device 200 extends from the body of the patient. The actuators 260 and 262 (which may be disposed on the second end portion 214 of the device 200) may then be activated to cause the extension members 230 and 240 to move to their expanded configurations. The lock members 270 and 275 may retain the extension members 230 and 240 in their expanded configurations and a medical procedure may be performed on the patient. Once the procedure is completed, the release members 280 and 285 (which may be disposed on the second end portion 214 of the device 200) may be activated to release the extension members 230 and 240 and allow the extension members 230 and 240 to move back to their first positions or configurations. The device 200 may then be removed from the body of the patient while the extension members 230 and 240 are in their refracted or smaller configurations.

Figure 4:
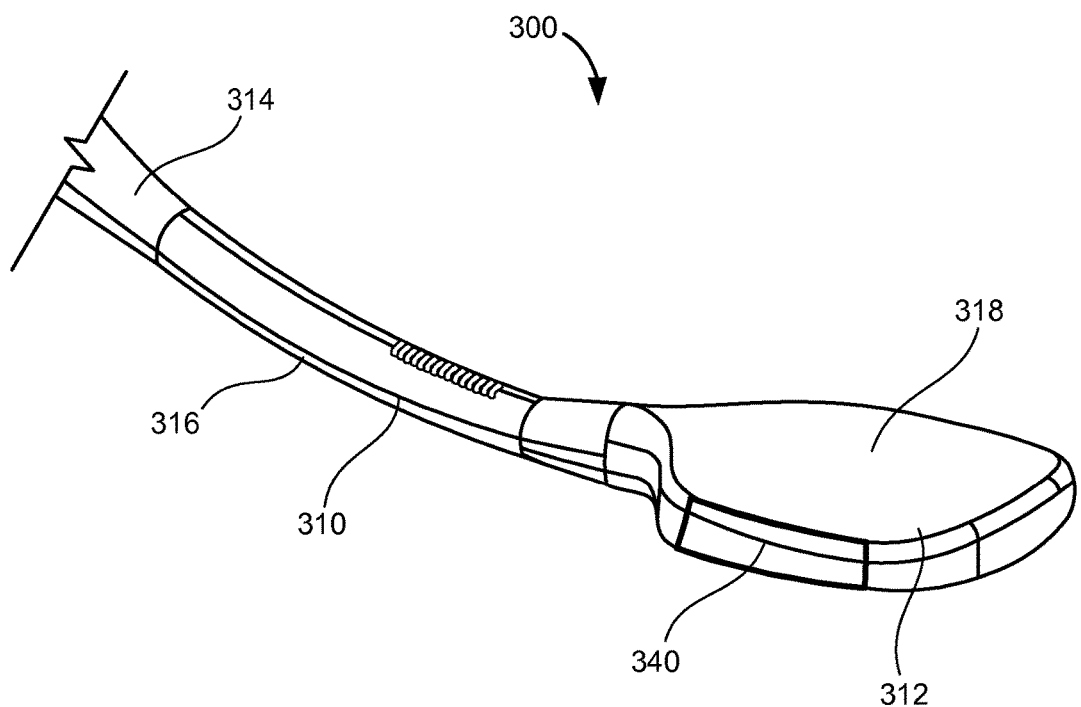
FIG. 4 is a perspective view of a medical device according to an embodiment of the invention.
Figure 5:
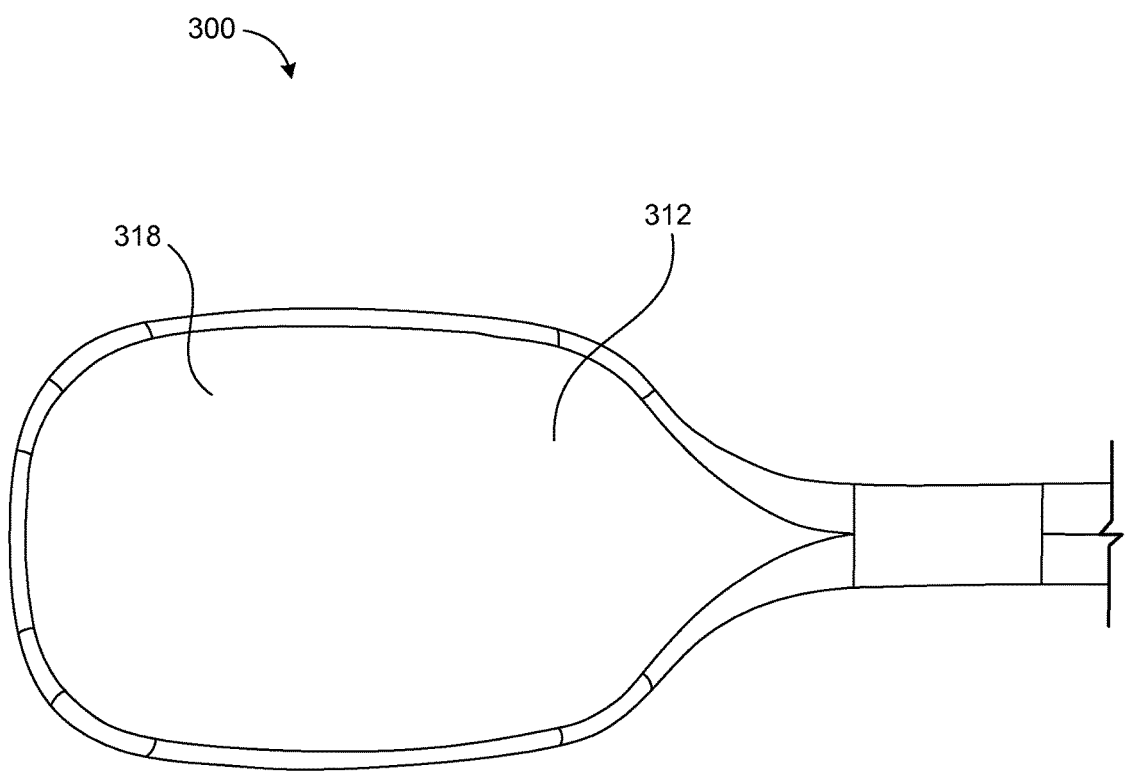
FIGS. 5 and 6 are top views of the medical device of FIG. 4.
Figure 6:
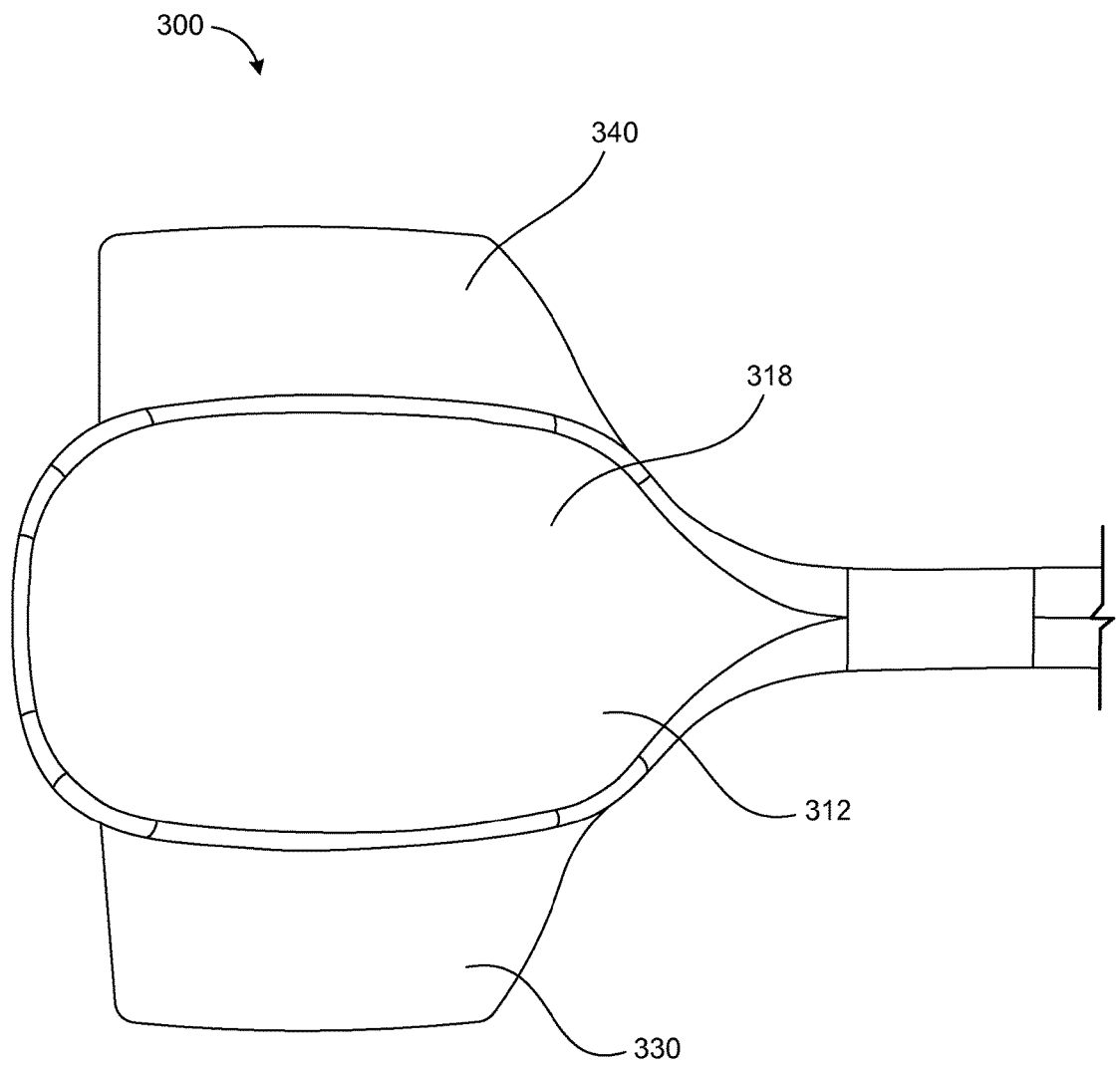

FIGS. 4-6 illustrate a medical device 300 according to another embodiment of the invention. The medical device 300 includes an elongated member 310. The elongate member has a first end portion 312 and a second end portion 314. The first end portion 312 is disposed opposite the second end portion 314. The elongate member 310 includes a shaft portion 316 that is disposed between the first end portion 312 and the second end portion 314. The shaft portion 116 is curved or bent (or non-linear).

The first end portion 312 of the medical device 300 includes surfaces that are configured to help maneuver the vagina to facilitate proper dissection in the pelvis. Specifically, flat surfaces 318 of the first end portion 112 are configured to contact and move the vagina around so that it is easier for dissection and placement of implants such as suspension implant or devices such as the sacrocolpopexy mesh arms. Flat or planar surfaces 318 of the first end portion 312 may also act as a backstop for suturing during abdominal or laparoscopic pelvic floor procedures. The flat surfaces 318 can also be used to spread the bodily tissue to facilitate suturing at a correct location. In some embodiments, the medical practitioner may use a first flat 318 surface to suture on anterior portions of the vagina and a second flat surface (disposed opposite the first flat surface 318) to suture on posterior portions of the vagina.

In the illustrated embodiment, extension members 330 and 340 are coupled to the first end portion 312. Specifically, the extension members 330 and 340 are movably or slidably coupled to the first end portion 312. The extension members 330 and 340 may move away from (or perpendicular to) a longitudinal axis of the elongate member 310 when the extension members 330 and 340 move from their first positions with respect to the first end portion 312 to their second positions with respect to the first end portion 312.

Figure 7:
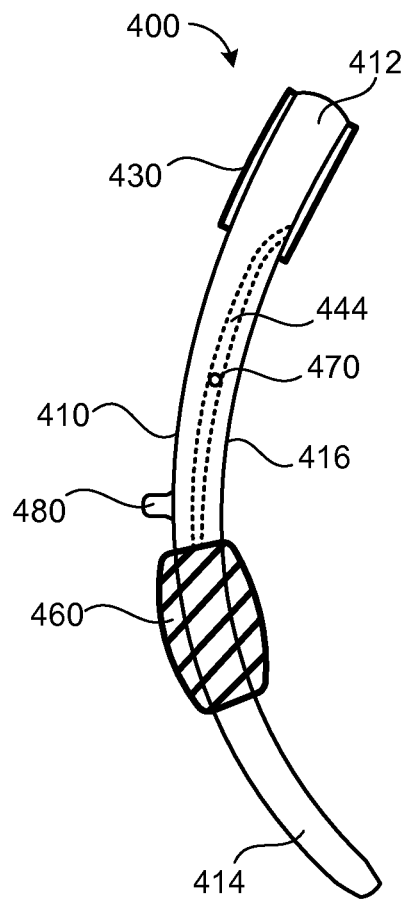
FIGS. 7 and 8 are side views of a medical device according to an embodiment of the invention.
Figure 8:
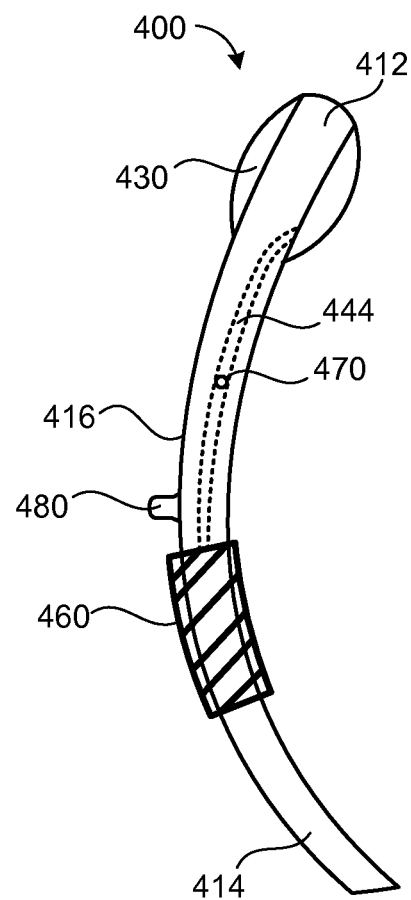

FIGS. 7 and 8 illustrate a medical device 400 in accordance with an embodiment of the invention. The medical device 400 includes an elongated member 410. The elongate member has a first end portion 412 and a second end portion 414. The first end portion 412 is disposed opposite the second end portion 414. The elongate member 410 includes a shaft portion 416 that is disposed between the first end portion 412 and the second end portion 414. The shaft portion 416 is curved or includes a curved portion.

The first end portion 412 of the medical device 400 includes surfaces that are configured to help maneuver the vagina to facilitate proper dissection in the pelvis. In some embodiments, the surfaces of the first end portion 412 are configured to contact and move the vagina around so that it is easier for dissection and placement of implants such as suspension implant or devices such as the sacrocolpopexy mesh arms. The surfaces of the first end portion 412 may also act as a backstop for suturing during abdominal/laparoscopic pelvic floor procedures. The surfaces can also be used to spread the bodily tissue to facilitate suturing at a correct location. In some embodiments, the medical practitioner may use a surface to suture on anterior portions of the vagina and a second surface to suture on posterior portions of the vagina.

The illustrated embodiment includes an extension member 430. In the illustrated embodiment, the extension member 430 is an inflatable member and is configured to move or inflate with respect to the first end portion 412. Accordingly, the device 400 may be inserted into the body of the patient when the extension member 430 is in one position (a retracted or smaller configuration) and may be moved to the other position (an expanded or larger configuration) when the device 400 is within the body of the patient. Additionally, in some embodiments, the device 400 may be removed from the body of the patient when the extension member 430 is in its retracted or smaller configuration. In some embodiments, the extension member 430 may be placed in more than two positions with respect to the first end portion 412. For example, in some embodiments, the extension member 430 may be placed in three, four, or more different positions with respect to the first end portion 412 (such as by varying the amount that the extension member 430 is inflated).

In some embodiments, the extension member 430 is formed of a compliant or expandable (stretchy) material. In other embodiments, the extension member is formed of a non-compliant material. In some embodiments, the inflatable member or portion may reinforced so as to help prevent punctures of the inflatable member or portion. For example, the inflatable member or portion may include a coating or a covering that is configured to help prevent punctures of the inflatable member or portion.

In some embodiments, the extension member 430 extends along at least two sides of the first end portion 412. For example, in some embodiments, the extension member 430 extends along a side portion and a distal end or terminal end portion of the first end portion 412. In other embodiments, the extension member 430 extends along a first side, a second side, and a terminal end of the first end portion 412.

In the illustrated embodiment, the extension member 430 surrounds the first end portion 412. In other embodiments, the extension member 430 is disposed on only a portion of the first end portion 412. For example, the extension member 430 may not completely surround the first end portion 412. In yet further embodiments, the medical device may include more than one inflatable member. Each inflatable member may be disposed on a portion of the first end portion of the elongate member.

In the illustrated embodiment, the device 400 includes an actuator 460. The actuator 460 is operatively coupled to the extension member 430. The actuator 460 may be moved or otherwise actuated to cause the extension member 430 to move from its first position with respect to the first end portion 412 to its second position with respect to the first end portion 412. Specifically, in the illustrated embodiment, the actuator 460 is a pump, such as a hand pump. The actuator 460 is in fluid communication with the extension member 430 via a lumen 444 defined by the elongate member 410. Accordingly, a physician may pump the actuator 460 to inflate the extension member 430. Actuator 460 may be a syringe or any other pressurized reservoir.

In the illustrated embodiment, the device 400 includes a valve member 470 disposed within the lumen 444. The valve member 470 is configured to help retain the extension member 430 in an expanded configuration. For example, in some embodiments, the valve member 470 is a one way valve such as a duckbill or other type of valve.

The device 400 includes a release member or release mechanism 480. The release member or release mechanism 480 is operatively coupled to the valve 470 and is configured to release the valve 470. Accordingly, the release member 480 may be actuated when valve 470 is retaining the extension member 460 in its expanded configuration (as illustrated in FIG. 8) to release valve 470 and allow the extension member 460 to assume its deflated configuration (as illustrated in FIG. 7).

In some embodiments, the extension member 430 is biased to its deflated configuration. The device 400 may be inserted into the body of the patient while the extension member 430 is in its refracted position. Specifically, the device 400 may be inserted into the body of the patient while the extension member 430 is in its retracted configuration such that the first end portion 412 of the device 400 is disposed within the body of the patient (such as within a vagina or other bodily opening of the patient) and the second end portion 414 of the device extends from the body of the patient. The actuator 460 (which may be disposed on the second end portion 414 of the device) may then be activated to cause the extension member 430 to expand. The valve 470 may retain the extension member 430 in its expanded configuration and a medical procedure may be performed on the patient. Once the procedure is completed, the release member 480 (which may be disposed on the second end portion 414 of the device) may be activated to allow the extension member 430 to move back to its deflated configuration. The device 400 may then be removed from the body of the patient while the extension member 430 is in its retracted or deflated configuration.

In some embodiments, the inflation of the extension member 430 causes the first end portion 412 to have a convex shape.

Figure 9:
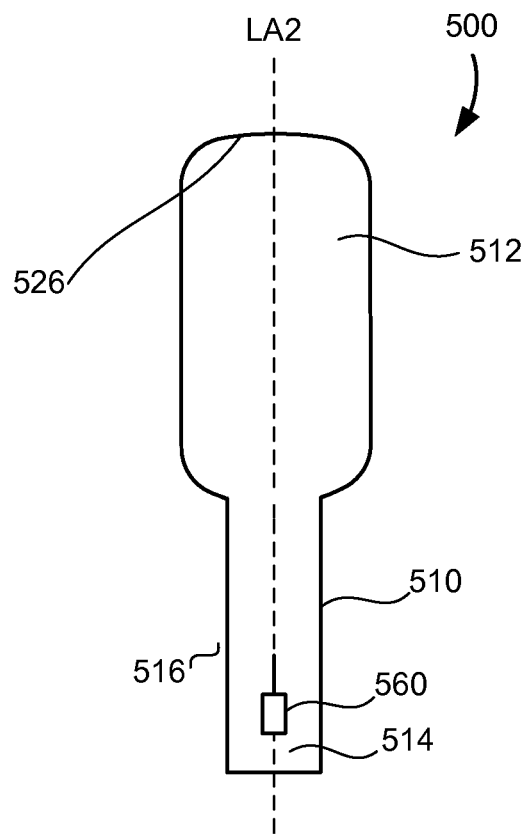
FIGS. 9 and 10 are top views of a medical device according to an embodiment of the invention.
Figure 10:
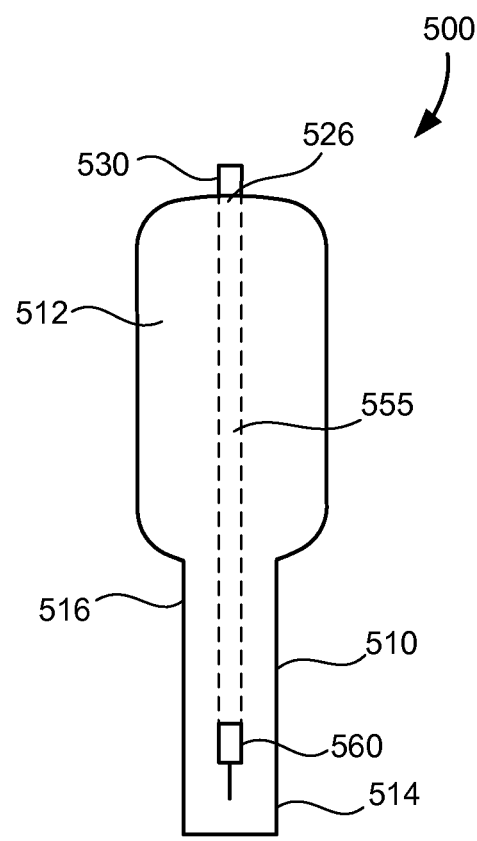

FIGS. 9 and 10 illustrate a medical device 500 according to an embodiment of the invention. The medical device 500 includes an elongated member 510. The elongate member 510 has a first end portion 512 and a second end portion 514. In some embodiments, the first end portion 512 is disposed opposite the second end portion 514. In some embodiments, the elongate member 510 includes a shaft portion 516 that is disposed between the first end portion 512 and the second end portion 514. In some embodiments, the shaft portion 516 is linear. In other embodiments, the shaft portion 516 is curved or includes a curved portion.

In some embodiments, the first end portion 512 of the medical device 500 includes surfaces that are configured to help maneuver the vagina to facilitate proper dissection in the pelvis. In some embodiments, flat surfaces of the first end portion 512 are configured to contact and move the vagina around so that it is easier for dissection and placement of implants such as suspension implant or devices such as the sacrocolpopexy mesh arms. Flat or planar surfaces of the first end portion 512 may also act as a backstop for suturing during abdominal or laparoscopic pelvic floor procedures. The flat surfaces can also be used to spread the bodily tissue to facilitate suturing at a correct location. In some embodiments, the medical practitioner may use a first flat surface to suture on anterior portions of the vagina and a second flat surface to suture on posterior portions of the vagina.

In the illustrated embodiment, the medical device includes an extension member 530. The extension member 530 is movably coupled to a terminal end portion 526 of the first end portion 512. In the illustrated embodiment, the terminal end portion 526 is at the distal most end or tip of the medical device 500. The extension member 530 is configured to move with respect to the first end portion 512. For example, the extension member 530 may move parallel to a longitudinal axis LA2 of the elongate member 510 when the extension member 530 moves from a first position with respect to the first end portion 512 to a second position with respect to the first end portion 512. In such embodiments, the length or size of the first end portion 512 and the extension member 530 may be varied. Specifically, the device 500 may be inserted into the body of the patient when the extension member 530 is in one position (a retracted or smaller configuration) and may be moved to the other position (an expanded or larger configuration) when the device 500 is within the body of the patient.

In some embodiments, the medical device 500 is configured to be inserted into a vagina of a patient and the extension member 530 is configured to contact and end portion of the vagina. In other embodiments, the extension member 530 is configured to contact a cervix or uterus of the patient. In yet other embodiments, the extension member 530 is configured to contact other portions or tissues of the body of the patient. In some embodiments, the extension member 530 is configured to contact a portion of the body of the patient and facilitate the movement or control of such portion of the body of the patient. For example, the cervix or uterus of the patient may be contacted by the extension member 530. The medial device 500 may be used to control or move the cervix or uterus via the extension member 530.

In the illustrated embodiment, the device 500 includes an actuator 560. The actuator 560 is operatively coupled to the extension member 530. The actuator 560 may be moved or otherwise actuated to cause the extension member 530 to move from its first position with respect to the first end portion 512 to its second position with respect to the first end portion 512. In some embodiments, the actuator 560 is configured to slide or move with respect to the elongate member 510 to move the extension member 530. For example, as illustrated in FIG. 9, the actuator 560 may be in a lower or down position and may be moved or slid to an up position (as illustrated in FIG. 10) to move the extension member 530 to its extended position.

In the illustrated embodiment, the actuator 560 is operatively coupled to the extension member 530 via a linkage 555. In other embodiments, other linkages or mechanisms are used to operatively couple the actuator 560 to the extension member 530.

In the illustrated embodiment, the linkage 555 is disposed within a cavity defined by the elongate member 510. In other embodiments, the linkage 555 is not disposed within a cavity defined by the elongate member 510.

In some embodiments, the device 500 may include a lock member or lock mechanism. The lock member or lock mechanism is operatively coupled to the actuator 560 or the extension member 530 and is configured to lock or help retain the extension member 530 in one of its first position and its second position with respect to the first end portion 512. In other embodiments, the actuator 560 is frictionally coupled within an opening defined by the elongate member 510. In such embodiments, the frictional coupling helps retain the extension member in one of its configurations or positions.

In some embodiments, the device 500 includes a release member or release mechanism. The release member or release mechanism is operatively coupled to the lock member or lock mechanism and is configured to release the lock member or lock mechanism from engagement with the actuator 560 or the first extension member 530. Accordingly, the release member may be actuated when lock member is retaining the extension member 530 in one of its first position and its second position to release the extension member 530 such that it is free to move between its first position and its second position. Device 500 may include a return spring or return member configured to return the extension member to its original unextended position when so desired.

In some embodiments, the extension member 530 is colored to facilitate the visualization of the extension member 530 during a medical procedure. In some embodiments, the extension member 530 is of a different color than the elongate member 510. In some embodiments, the extension member 530 is blue in color.

Figure 11:
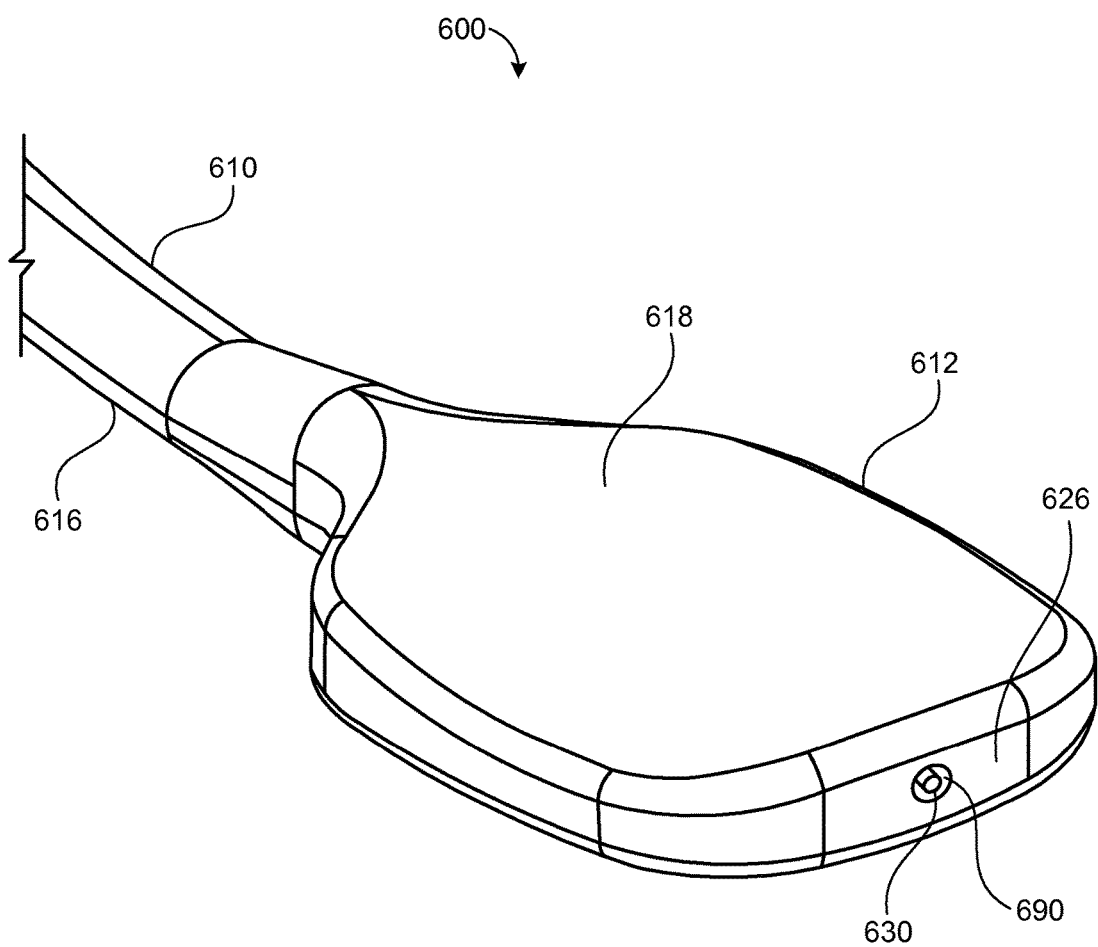
FIGS. 11 and 12 are perspective views of a portion of a medical device according to an embodiment of the invention.
Figure 12:
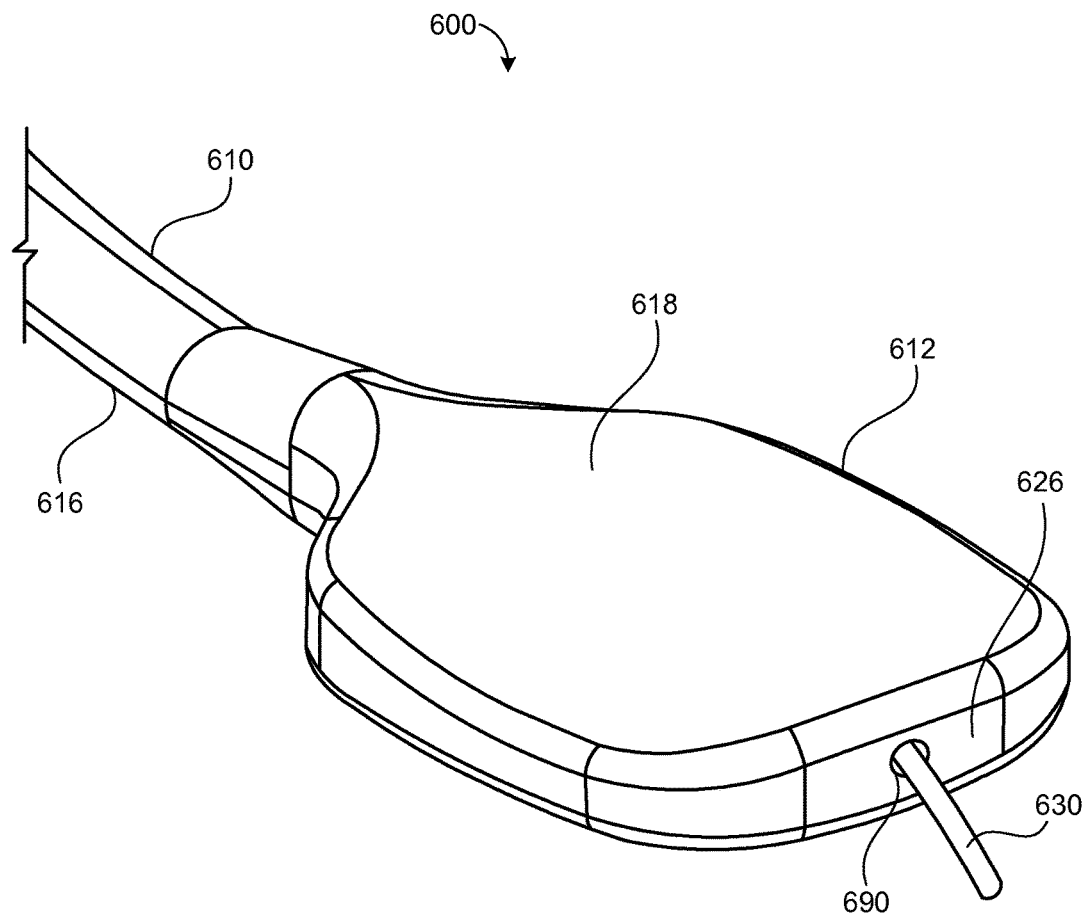

FIGS. 11 and 12 illustrate a distal end portion of a medical device 600 according to an embodiment of the invention. The medical device 600 includes an elongated member 610. The elongate member 610 has a first end portion 612 and a second end portion (not illustrated). The first end portion 612 is disposed opposite the second end portion. The elongate member 610 includes a shaft portion 616 that is disposed between the first end portion 612 and the second end portion 314. The shaft portion 616 may be curved or bent (or non-linear).

The first end portion 612 of the medical device 600 includes surfaces that are configured to help maneuver the vagina to facilitate proper dissection in the pelvis. Specifically, flat surfaces 618 of the first end portion 612 are configured to contact and move the vagina around so that it is easier for dissection and placement of implants such as suspension implant or devices such as the sacrocolpopexy mesh arms. Flat or planar surfaces 618 of the first end portion 612 may also act as a backstop for suturing during abdominal or laparoscopic pelvic floor procedures. The flat surfaces 618 can also be used to spread the bodily tissue to facilitate suturing at a correct location. In some embodiments, the medical practitioner may use a first flat 618 surface to suture on anterior portions of the vagina and a second flat surface (disposed opposite the first flat surface 318) to suture on posterior portions of the vagina.

In the illustrated embodiment, an extension member 630 is coupled to the first end portion 612. Specifically, the extension member 630 is movably or slidably coupled to the distal most end portion (or a terminal end portion) of the first end portion 612. The extension member 630 moves in a direction substantially parallel to a longitudinal of the elongate member 610. As best illustrated in FIG. 11, when the extension member 630 is in a retracted position, the extension member 630 (or at least a portion of the extension member 630) is disposed within a cavity 690 defined by the first end portion 612. As best illustrated in FIG. 12, when the extension member 630 is in an extended position, the extension member 630 (or the portion of the extension member 630) is disposed outside of the cavity 690 defined by the first end portion 612 of the elongate member 610.

Figure 13:
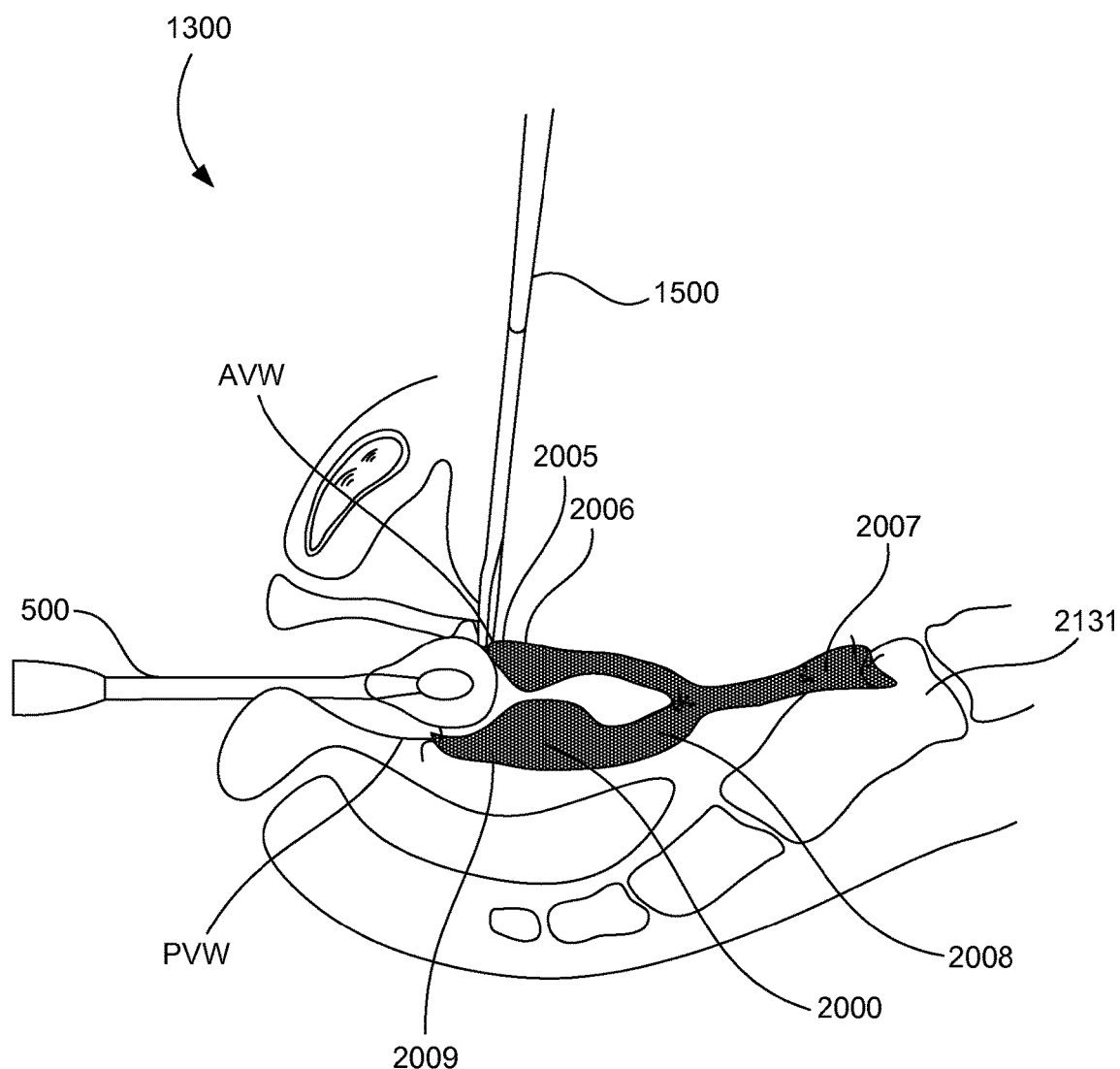
FIG. 13 is a schematic illustration of a medical device according to an embodiment of the invention disposed within a body of a patient.

FIG. 13 schematically illustrates a medical device 600 disposed within a body of a patient. The medical device 600 may be similar to the other devices disclosed herein. As illustrated, in some embodiments, the implant 2000 may be a Y-shaped implant. In such embodiments, the Y-shaped implant 2000 includes a first elongated member 2006 and a second elongated member 2008 that extends from a midportion of the first elongated member 2006. A suturing tool 1500 may be used to couple a first end portion 2005 of the first elongated member 2006 to an anterior vaginal wall AVW. A second end portion 2007 of the first elongated member 2006 can be attached to a sacrum 2131 of the patient or tissues disposed proximate the sacrum 2131 of the patient. A first end portion 2009 of the second elongated member 2008 is attached to a posterior vaginal wall PVW. In the illustrated embodiment, the implant 2000 may form such a Y-shaped implant as the first elongated member 2006 may be coupled to the second elongated member 2008 at or near the junction of the members (for example, near the vaginal apex of the patient). As illustrated, the implant 2000 may surround or cup the vaginal apex.

Figure 14:
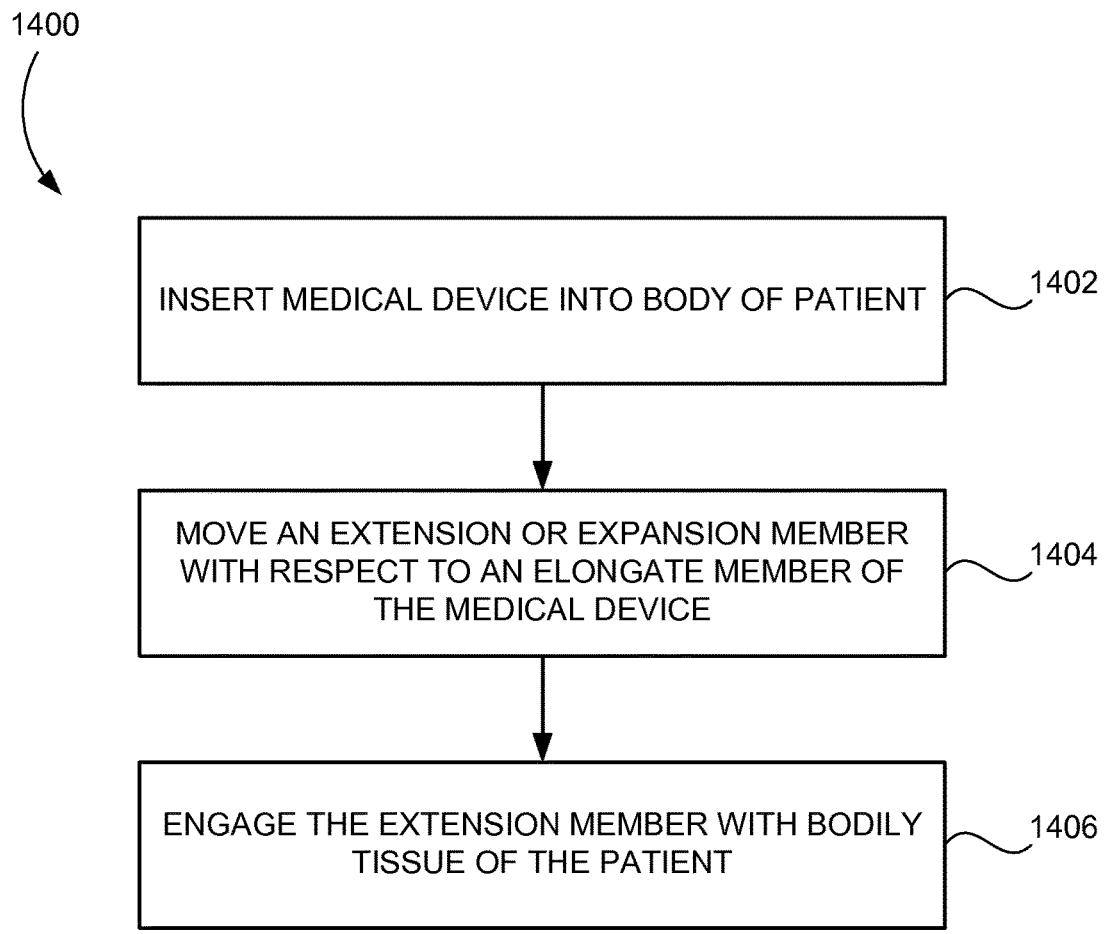
FIG. 14 is a flow chart of a method according to an embodiment of the invention.

FIG. 14 is a method 1400 according to an embodiment of the invention. At 1402, a medical device is inserted into a body of a patient. In some embodiments, the medical device is inserted into a vagina of the patient. In other embodiments, the medical device is inserted into other portions of the body of the patient. For example, in some embodiments, the medical device may be inserted into a rectum or gastrointestinal tract of the patient.

In some embodiments, the medical device is inserted into the body while the device is in a collapsed or contracted configuration. For example, the device may be inserted while an expansion member is in a first or retracted position with respect to an elongate member of the medical device.

At 1404, the medical device may be placed in an expanded configuration. For example, while the device is disposed within the body of the patient, the expansion member may be moved to an extended configuration. In some embodiments, the size or width of the medical device is larger when the expansion member is in its extended configuration. In some embodiments, actuation of an actuator causes the expansion member to move from its retracted position to its expanded position.

At 1406, the extension member is contacted with bodily tissue. In some embodiments, the contacting of the bodily tissue causes the portion of the body to expand. For example, in one embodiment, the vagina of the patient is expanded when the tissue is contacted. In other embodiments, a cervix or uterus may be contacted and manipulated.

In some embodiments, a medical procedure may occur while the medical device is disposed within the body of the patient. For example, in some embodiments, a pelvic implant, such as a pelvic support mesh, may be placed within the body of the patient while the medical device is within the body of the patient.

The medical device may then be placed in its smaller or collapsed configuration by moving the expansion member back to its retracted position. The device may then be removed from the body of the patient.

In some embodiments, a medical device includes an elongate member having a first end portion and a second end portion; an extension member movably coupled to the first end portion of the elongate member; and an actuation member disposed on the second end portion of the elongate member and operatively coupled to the extension member to move the extension member from a first position with respect to the first end portion of the elongate member to a second position with respect to the elongate member.

In some embodiments, the first end portion of the elongate member has a first side portion, a second side portion opposite the first side portion, and a terminal portion, the extension member being movably coupled to the first side portion. In some embodiments, the first end portion of the elongate member has a first side portion, a second side portion opposite the first side portion, and a terminal portion, the extension member being movably coupled to the terminal portion. In some embodiments, the first end portion of the elongate member has a first side portion, a second side portion opposite the first side portion, and a terminal portion, the extension member being a first extension member, the first extension member being movably coupled to the first side portion, the medical device further including a second extension member movably coupled to the second side portion.

In some embodiments, the first end portion of the elongate member has a first side portion, a second side portion opposite the first side portion, and a terminal portion, the extension member being a first extension member, the first extension member being movably coupled to the first side portion, the medical device further including a second extension member movably coupled to the second side portion; and a third extension member movably coupled to the terminal portion.

In some embodiments, the elongate member defines a longitudinal axis, the extension member being configured to move in a direction substantially perpendicular to the longitudinal axis when the extension member is moved from its first position to its second position. In some embodiments, the elongate member defines a longitudinal axis, the extension member being configured to move in a direction substantially parallel to the longitudinal axis when the extension member moves from its first position to its second position.

In some embodiments, the device includes a lock member operatively coupled to the extension member, the lock member being configured to help retain the extension member in at least one of its first position and its second position.

In some embodiments, the device includes a lock member operatively coupled to the extension member, the lock member being configured to help retain the extension member in at least one of its first position and its second position; and a release member operatively coupled to the lock member, the release member being configured release the lock member.

In some embodiments, the second end portion is a handle portion and the actuation member is configured to slide along a portion of the handle portion.

In some embodiments, the first end portion of the elongate member defines a cavity, a portion of the extension member being disposed within the cavity when the extension member is in its first configuration, the portion of the extension member being disposed outside of the cavity when the extension member is in its second position. In some embodiments, the actuation member is configured to move the extension member to a third position with respect to the elongate member, the third position being different than the first position and the second position. In some embodiments, the extension member includes an inflatable member.

In some embodiments, a medical device includes an elongate member having a first end portion and a second end portion, the first end portion of the elongate member having a first side portion, a second side portion opposite the first end portion, and a terminal portion, the first end portion defining a cavity; an extension member movably coupled to the terminal portion of the first end portion of the elongate member, a portion of the extension member being disposed within the cavity when the extension member is in its first position, the portion of the extension member being disposed outside of the cavity when the extension member is in its second position; and an actuation member disposed on the second end portion of the elongate member and operatively coupled to the extension member to move the extension member from a first position with respect to the first end portion of the elongate member to a second position with respect to the elongate member.

In some embodiments, the actuation member is configured to slide along a portion of the second end portion. In some embodiments, the actuation member is configured to move the extension member to a third position with respect to the elongate member, the third position being different than the first position and the second position. In some embodiments, the elongate member defines a longitudinal axis, the extension member being configured to move in a direction substantially parallel to the longitudinal axis when the extension member moves from its first position to its second position.

In some embodiments, the extension member being a first extension member, the medical device further includes a second extension member movably coupled to the first side portion of the first end portion of the elongate member.

In some embodiments, a method includes inserting a medical device into a body of a patient, the medical device including an elongate member having a first end portion and a second end portion, an extension member movably coupled to the first end portion of the elongate member and configured to move from a first position with respect to the elongate member to a second position with respect to the elongate member; moving an actuator of the medical device to move the extension member from its first position to its second position; and engaging the extension member of the medical device with bodily tissue of the patient.

In some embodiments, the inserting includes inserting the medical device into a vagina of the patient. In some embodiments, the engaging includes engaging the extension member of the medical device with a uterus of the patient.

While certain features of the described implementations have been illustrated as described herein, many modifications, substitutions, changes and equivalents will now occur to those skilled in the art. For example, a medical device may have any number of extension members and the different extension members may extend in any number of directions with respect to the longitudinal axis of the medical device. It is, therefor, to be understood that the appended claims are intended to cover all such modifications and changes as fall within the scope of the embodiments.

What is claimed is:

1. A medical device configured to manipulate a portion of a body of a patient, comprising:

an elongate member having a first end portion and a second end portion, the first end portion having a first planar surface and a second planar surface opposite to the first planar surface;

a first extension member movably coupled to the first end portion of the elongate member, the first extension member having a planar surface;

a second extension member movably coupled to the first end portion of the elongate member, the second extension member having a planar surface; and an actuation member disposed on the second end portion of the elongate member and operatively coupled to the first extension member and the second extension member, the actuation member being movable with respect to the elongate member, wherein, when the actuation member moves towards a longitudinal axis of the elongate member, the first extension member and the second extension member move from a retracted position to an extended position in a direction away from the longitudinal axis of the elongate member, the first extension member and the second extension member configured to extend a width of the first end portion from a first width in which the first extension member and the second extension member are within the retracted position to a second width in which the first extension member and the second extension member are within the extended position, the second width being larger than the first width.

2. The medical device of claim 1, wherein the first end portion of the elongate member has a first side portion, a second side portion opposite the first side portion, and a terminal portion, the first extension member being movably coupled to the first side portion, the second extension member being movably coupled to the second side portion.

3. The medical device of claim 1, wherein the actuation member includes a first actuator operatively coupled to the first extension member, and a second actuator operatively coupled to the second extension member.

4. The medical device of claim 3, wherein the second end portion of the elongate member has a first side portion, and a second side portion opposite the first side portion, the first actuator being movably coupled to the first side portion, the second actuator being movably coupled to the second side portion.

5. The medical device of claim 1, wherein the first extension member and the second extension member are configured to move in a direction substantially perpendicular to the longitudinal axis of the elongate member.

6. The medical device of claim 1, wherein the actuator includes a wheel and a linkage.

7. The medical device of claim 1, further comprising:
a lock member operatively coupled to the first extension member, the lock member being configured to help retain the first extension member in the extended position.

8. The medical device of claim 7, further comprising:
a release member operatively coupled to the lock member, the release member being configured release the lock member.

9. The medical device of claim 1, wherein the elongate member includes a shaft portion disposed between the first end portion and the second end portion, the shaft portion including a curved cylindrical portion.

10. The medical device of claim 1, wherein the actuation member is configured to move the first extension member and the second extension member to a middle position with respect to the elongate member, the middle position being different than the retracted position and the extended position.

11. The medical device of claim 1, wherein the first extension member and the second extension member are spring biased to the retracted position.

12. A medical device configured to manipulate a vagina of a patient, the medical device comprising:

an elongate member having a first end portion, a second end portion, and a curved shaft disposed between the first end portion and the second end portion, the first end portion configured to be inserted into the vagina of the patient, the second end portion configured to be disposed outside a body of the patient, the elongate member having a lumen, a valve disposed within the lumen, and a release member operatively coupled to the valve, the release member being disposed on the second end portion of the elongate member;

an extension member movably coupled to the first end portion of the elongate member, the extension member including an inflatable member configured to inflate to an expanded state with respect to the first end portion, the inflatable member extending along at least two sides of the first end portion; and an actuation member fluidly coupled to the inflatable member, the actuation member including a pump configured to transfer fluid to the inflatable member to inflate the inflatable member, the pump being mounted on the second end portion of the elongate member, wherein, when the inflatable member is inflated, the valve is configured to retain the inflatable member within the expanded state, and, when the release member is activated, the valve is released to transition the inflatable member to a deflated state.

13. The medical device of claim 12, wherein the inflatable member surrounds a circumference of the first end portion of the elongate member.

* * * * *